US009125622B2

(12) United States Patent
Kitamura

(10) Patent No.: US 9,125,622 B2
(45) Date of Patent: Sep. 8, 2015

(54) DIAGNOSIS ASSISTING APPARATUS, CORONARY ARTERY ANALYZING METHOD AND RECORDING MEDIUM HAVING A CORONARY ARTERY ANALYZING PROGRAM STORED THEREIN

(75) Inventor: Yoshiro Kitamura, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 297 days.

(21) Appl. No.: 13/035,471

(22) Filed: Feb. 25, 2011

(65) Prior Publication Data

US 2011/0218427 A1 Sep. 8, 2011

(30) Foreign Application Priority Data

Mar. 8, 2010 (JP) ................................. 2010-050009

(51) Int. Cl.
*A61B 6/00* (2006.01)
*A61B 5/02* (2006.01)
*G06T 7/00* (2006.01)

(52) U.S. Cl.
CPC ........... *A61B 6/5217* (2013.01); *A61B 5/02007* (2013.01); *A61B 6/5205* (2013.01); *A61B 6/5211* (2013.01); *A61B 5/02* (2013.01); *G06T 7/0016* (2013.01); *G06T 2207/10076* (2013.01); *G06T 2207/20072* (2013.01); *G06T 2207/30048* (2013.01); *G06T 2207/30101* (2013.01); *G06T 2207/30172* (2013.01)

(58) Field of Classification Search
USPC ......................................... 600/407; 382/128
See application file for complete search history.

(56) References Cited

U.S. PATENT DOCUMENTS

| 6,243,437 | B1 * | 6/2001 | Hu et al. ............................. 378/8 |
| 6,990,222 | B2 * | 1/2006 | Arnold ........................... 382/131 |
| 7,338,452 | B2 | 3/2008 | Shiina et al. |
| 7,346,203 | B2 * | 3/2008 | Turek et al. .................... 382/131 |
| 7,558,611 | B2 * | 7/2009 | Arnold et al. ................. 600/407 |

(Continued)

FOREIGN PATENT DOCUMENTS

| JP | 2004-329550 | 11/2004 |
| JP | 2009-195561 | 9/2009 |

OTHER PUBLICATIONS

Medical Physiology by Walter F. Boron and Emile L. Boulpaep pub. Elsevier Health Sciences 2008.*

(Continued)

*Primary Examiner* — Katherine Fernandez
*Assistant Examiner* — Michael Kellogg
(74) *Attorney, Agent, or Firm* — Young & Thompson

(57) ABSTRACT

A plurality of sets of volume data, each of which represent the state of a beating heart in different phases, are obtained. Coronary artery regions are extracted from at least two sets of volume data from among the obtained sets of volume data. A plurality of analysis points are set in each extracted coronary artery region. Correlations are established among analysis points set at the same anatomical positions within the coronary artery regions. Index values that indicate the character of plaque are calculated at each analysis point within all of the coronary artery regions. The character of plaque is evaluated at positions within the coronary artery regions, by integrating the index values calculated at the analysis points corresponding to each of the positions. The evaluation results regarding the character of plaque at each of the positions within the coronary artery regions are output, correlated with information regarding the positions.

8 Claims, 11 Drawing Sheets

(56) References Cited

U.S. PATENT DOCUMENTS

| 7,646,903 B2 | 1/2010 | Kaftan et al. |
| 2009/0136107 A1 | 5/2009 | Arnold et al. |

OTHER PUBLICATIONS

JP Office Action dated Jan. 17, 2012, with English Translation, Application No. 2010-050009.

Szymczak et al., "Coronary vessel trees from 3D imagery: A topological approach", Medical Image Analysis 10 (2006) 548-559, College of Computing, Georgia Tech, 85 5th street NW, Atlanta, GA 30332, Received Oct. 12, 2005; received in revised form Apr. 18, 2006; accepted May 5, 2006, Available online Jun. 22, 2006 www.sciencedirect.com.

Extended European Search Report—EP 11 15 5534—Jan. 16, 2013.

Chinese Office Action, dated Dec. 3, 2014, in corresponding Chinese Patent Application No. 201110055519.6.

\* cited by examiner

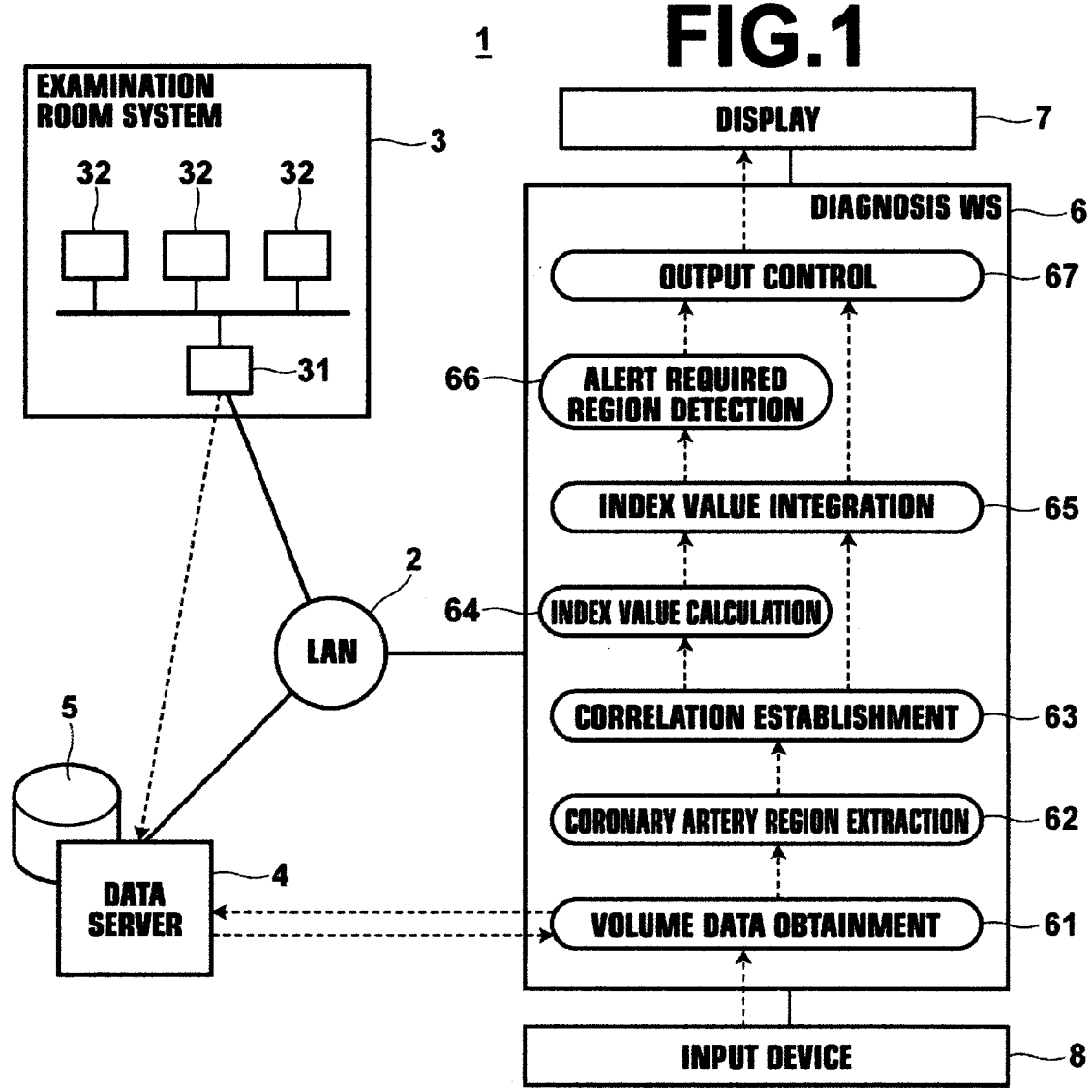
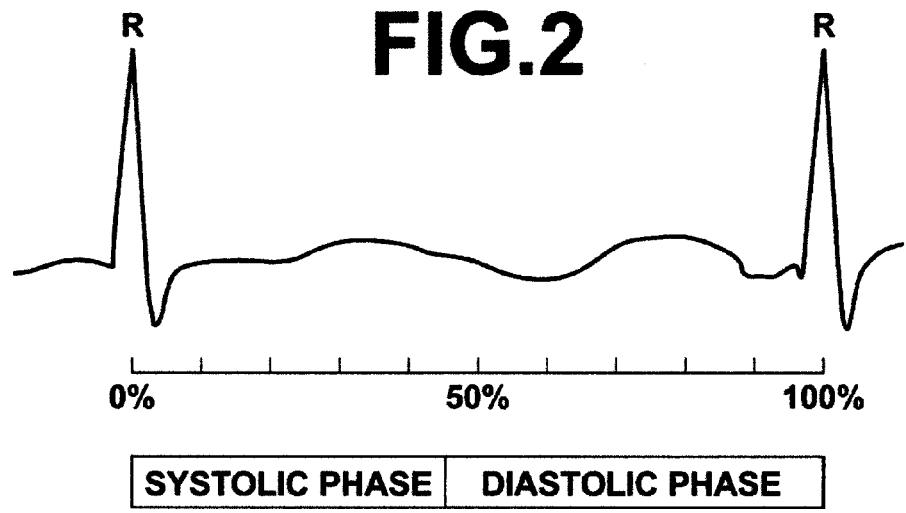

BASE OF HEART $S_{ref}$ (AORTIC VALVE)
$S_{ref}$ (MITRAL VALVE)
$S_{ref}$ (APEX OF HEART)

—— R-R 30%
----- R-R 70%

DIAGNOSIS ASSISTING APPARATUS, CORONARY ARTERY ANALYZING METHOD AND RECORDING MEDIUM HAVING A CORONARY ARTERY ANALYZING PROGRAM STORED THEREIN

BACKGROUND OF THE INVENTION

1. Field of the Invention

The present invention is related to a method and an apparatus for assisting diagnosis by physicians by analyzing the states of coronary arteries based on there dimensional data. The present invention is also related to a recording medium in which a program that causes at least one computer to execute the diagnosis assisting method is recorded.

2. Description of the Related Art

Apparatuses and software programs that analyze the states of organs and blood vessels based on three dimensional image data (volume data) obtained by CT (Computed Tomography) examinations are being provided as tools for assisting image diagnosis by physicians. Cardiac function analyzing functions and coronary artery analyzing functions are widely utilized as functions for assisting diagnosis of the heart. With respect to the cardiac artery analyzing functions, Japanese Unexamined Patent Publication No. 2009-195561 discloses an apparatus that extracts the intravascular regions and soft plaque candidates from a single three dimensional X ray CT image, and displays the extracted soft plaque regions overlapped on the three dimensional CT image.

A plurality of sets of volume data that represents the state of the heart at different points in time are necessary in order to understand the movement of the heart (temporal changes) when analyzing cardiac functions. For this reason, a plurality of sets of volume data having different phases within a single cardiac cycle are generally obtained during examinations of the heart. Meanwhile, the state of stenosis does not change dramatically within a single cardiac cycle. For this reason, analysis of coronary arteries is performed employing a single set of volume data, as described in Japanese Unexamined Patent Publication No. 2009-195561.

It is desirable to employ a set of volume data which is obtained when the movement of cardiac muscles is minimal when analyzing coronary arteries. Sets of volume data which are obtained when the movement of cardiac muscles is great often include problems, such as motion artifacts and faulty contrast caused by shifts in the injection timing of contrast agents, resulting in accurate extraction of coronary artery regions becoming difficult. Commonly, it is considered that sets of volume data obtained during a middiastolic state are favorable to be used for analyzing coronary arteries.

However, there are differences in the shapes of hearts and the movement of the cardiac muscles among individuals. In addition, the beating of the heart is accompanied by twisting of the cardiac muscles. Therefore, the movement of the cardiac muscles differs in the periphery of the left coronary artery and in the periphery of the right coronary in the same heart. For this reason, it is not always the case that a set of volume data that represents the heart in a middiastolic state is optimal as data to be utilized to analyze coronary arteries. In fact, there are reports that sets of volume data obtained during telesystolic states are favorable to analyze right coronary arteries and to analyze states during high heart rates. Therefore, it is difficult to determine a single optimal phase for analysis. Based on these circumstances, selection of volume data (selection of an optimal phase) to be employed to analyze coronary arteries is currently being performed based on visual evaluations by physicians and technicians.

As described above, it had been conventionally necessary to select one specific phase to perform coronary artery analysis. It is difficult for a computer to automatically select an optimal phase, and it had been necessary to rely on the visual evaluations of physicians and technicians. There is a problem that accurate evaluation results cannot be obtained if the selection of an optimal phase is erroneous. In view of these circumstances, it is an object of the present invention to provide an apparatus and a method which are capable of constantly accurately analyzing and evaluating the stenosis state of coronary arteries. It is another object of the present invention to provide a recording medium having a program, that causes at least one computer to execute the method of the present invention, stored therein.

A diagnosis assisting apparatus of the present invention is equipped with a volume data obtaining means, a coronary artery region extracting means, a correlation establishing means, an index value calculating means, an index value integrating means, and an output control means, as means for achieving the above objective. A coronary artery analyzing program which is stored in a recording medium of the present invention is a software program that causes one or a plurality of computers to function as the volume data obtaining means, the coronary artery region extracting means, the correlation establishing means, the index value calculating means, the index value integrating means, and the output control means. The coronary artery analyzing program is generally constituted by a plurality of program modules. The function of each of the means listed above is performed by one or a plurality of the program modules. The group of program modules is provided to users by being recorded in storage media such as CD-ROM's and DVD's, by being recorded in a storage unit attached to a server computer in a downloadable state, or by being recorded in network storage (non transitory storage) in a downloadable state. A coronary artery analyzing method of the present invention is a method that analyzes the states of coronary arteries, by executing the processes of the volume data obtaining means, the coronary artery region extracting means, the correlation establishing means, the index value calculating means, the index value integrating means, and the output control means, which will be described below.

The volume data obtaining means obtains a plurality of sets of volume data, each of which represent the state of a beating heart in different phases. In the case that the obtained sets of volume data are to be employed to analyze cardiac functions, it is preferable for the volume data obtaining means to obtain volume data which are generated and output by a modality, such as a CT apparatus, for all phases during a single cardiac cycle. Meanwhile, in the case that the obtained sets of volume data are to be employed only to analyze coronary artery functions, it is not necessary to obtain volume data for all phases, and volume data that represent phases within predetermined ranges may be obtained.

The coronary artery region extracting means extracts coronary artery regions from at least two sets of volume data from among the sets of volume data obtained by the volume data obtaining means. The coronary artery region extracting means may perform extracting processes with respect to all sets of volume data supplied by the volume data obtaining means. Alternatively, the coronary artery region extracting means may perform the extracting processes only with respect to sets of volume data that represent the states of specific phases, from among the sets of volume data supplied by the volume data obtaining means. It is preferable for the process to extract the coronary artery regions to be executed with respect to one or a plurality of sets of volume data that represents the heart in a telesystolic state, and one or a plurality of sets of volume data that represents the heart in a middiastolic state, from the viewpoint of analysis accuracy.

The correlation establishing means sets a plurality of analysis points in each of the extracted coronary artery regions, and establishes correlations among the analysis points, which are set at the same anatomical positions, within the plurality of coronary artery regions. The points which are set as analysis points may be those which are extracted by the coronary artery region extracting means as points that represent the paths of the coronary arteries, may be selected from among such points. Note that the expression "the same anatomical positions" refers to positions within ranges which are recognized as the same portions during diagnosis, and it is not necessary for the positions to match completely.

The index value calculating means calculates index values that indicate the character of plaque at each of the analysis points within all of the plurality of coronary artery regions. Here the expression "character of plaque" refers to whether plaque is present, the percentage occupied by plaque (stenosis rate), the properties of plaque (such as whether the plaque is unstable), components of plaque, etc. The index values are calculated based on at least one of the diameter, the area, and the signal values of either the coronary artery region, the intravascular regions of coronary arteries, or both. A plurality of index values will be calculated with respect to points which are at the same anatomical positions by the processes executed by the index value calculating means.

The index value integrating means evaluates the character of plaque at positions within the coronary artery regions, by integrating the index values which are calculated at the plurality of analysis points corresponding to each of the positions. For example, the index value integrating means may evaluate the character of plaque based on a total sum of a plurality of index values. Alternatively, the index value integrating means may calculate weighted averages of the plurality of index values by multiplying the index values by weighting coefficients which are set for each of the phases, and evaluate the character of plaque based on the values of the weighted averages. The index value integrating means evaluates the character of plaque based on a plurality of index values. Therefore, the influence imparted by inaccurate values to the evaluation results is lessened, even in cases that some of the plurality of the index values are inaccurate.

In the case that the weighted averages of the index values are calculated by the index value integrating means, it is preferable for the weighting coefficients that the index values calculated for analysis points corresponding to positions within a right coronary artery region are multiplied by to be set higher for the telesystolic phase than for other phases. Meanwhile, it is preferable for the weighting coefficients that the index values calculated for analysis points corresponding to positions within a left coronary artery region are multiplied by to be set higher for the middiastolic phase than for other phases. By setting the weighting coefficients in this manner, the influence imparted on the evaluation results by index values calculated from sets of volume data obtained during periods when the movement of the cardiac muscles is small can be relatively increased. Thereby, the accuracy of evaluations can be improved.

The output control means outputs the evaluation results regarding the character of plaque at each of the positions within the coronary artery regions, correlated with information regarding the positions. Recording of the evaluation results into recording media, and output of the evaluation results to a printer may be considered as manners in which the evaluation results are output, in addition to display on a screen. In the case that the evaluation results are displayed on a screen, it is preferable for the evaluation results for each position to be displayed such that they overlap images that represent the coronary artery region.

A configuration may be adopted, in which the diagnosis assisting apparatus further comprises alert required region detecting means, for detecting alert required regions based on the evaluation results regarding the character of plaque in addition to the aforementioned means. In this case, the output control means displays or prints the detected alert required regions in a discernable manner during output of the evaluation results. Here, the expression "alert required regions" refers to regions at which careful observation is thought to be required during diagnosis. In other words, the alert required regions are regions which have possibilities of being factors that may cause serious disorders. The alert required region detecting means may detect regions having index values that indicate a stenosis rate greater than a predetermined threshold value as alert required regions. Alternatively, the alert required region detecting means may detect regions having index values that indicate instability of plaque greater than a predetermined threshold value as alert required regions. Further, the alert required region detecting means may detect regions having index values that indicate a stenosis rate greater than a predetermined threshold value and index values that indicate instability of plaque greater than a predetermined threshold value as alert required regions. If the alert required region detecting means is provided, regions of interest can be focused on in advance, to reduce the burden of observations placed on physicians, thereby improving efficiency of diagnosis.

According to the present invention, it is not necessary to select specific phases to perform analysis. Accordingly, the burden of selecting phases is not placed on physicians or technicians. In addition, a plurality of sets of volume data that represent states in different phases are utilized to perform analysis. Therefore, the influence of sets of volume data having poor image quality can be reduced. As a result, great errors do not occur in the analysis results, and constantly uniform accuracy in analysis can be guaranteed.

BRIEF DESCRIPTION OF THE DRAWINGS

FIG. 1 is a diagram that illustrates the schematic structure of a diagnosis assisting apparatus according to an embodiment of the present invention.

FIG. 2 is a diagram for explaining imaging synchronized with ECG's.

DESCRIPTION OF THE PREFERRED EMBODIMENTS

Figure 3A:
FIG. 3A is a diagram that illustrates a heart at a phase R-R0%.

Hereinafter, embodiments of a diagnosis assisting apparatus, a coronary artery analyzing method, and a recording medium in which a coronary artery analyzing program is recorded of the present invention will be described with reference to the attached drawings.

FIG. 1 illustrates the schematic structure of a hospital system 1 that includes a diagnosis assisting apparatus according to an embodiment of the present invention. The hospital system 1 is constituted by: an examination room system 3; a data server 4; and a diagnosis workstation 6 (WS 6); which are connected to each other via a local area network 2 (LAN 2).

The examination room system 3 is constituted by: various modalities 32 for imaging subjects; and an examination room workstation 31 (WS 31) for confirming and adjusting images output from each modality. Examples of the modalities 32 include: an X ray imaging apparatus; an MSCT (Multi Slice Computed Tomography) apparatus; a DSCT (Dual Source Computed Tomography) apparatus; an MRI (Magnetic Resonance Imaging) apparatus, and a PET (Positron Emission Tomography) apparatus. The modalities 32 are apparatuses that comply with DICOM (Digital Imaging and Communication in Medicine) standards that appends data to the obtained sets of volume data and outputs them as DICOM files.

The files output by the modalities 32 are forwarded to the data server 4 by the examination room WS 31. The data server 4 is a comparatively high processing performance computer equipped with a high performance processor and a high capacity memory, in which a software program that provides the functions of a DBMS (Database Management Server) is installed. The software program is stored in the memory, and executed by the processor. The data server 4 causes the volume data sent from the examination room WS 31 to be stored in a high capacity storage 5. In addition, the data server selects files that satisfy search conditions from among the plurality of files stored in the high capacity storage 5, in response to search requests from the diagnosis WS 6. Then, the data server 4 sends the selected files to the diagnosis WS 6.

The diagnosis WS 6 is a general purpose workstation equipped with a normal processor, memory and storage, in which a diagnosis assisting program is loaded. The diagnosis assisting program is installed in the diagnosis WS 6 from a recording medium such as a DVD, or by being downloaded from a server computer on a network. In addition, a display 7, and input devices 8 such as a keyboard and a mouse are connected to the diagnosis WS 6.

The diagnosis assisting program installed in the diagnosis WS 6 is constituted by a group of program modules that realize various functions. Among the program modules is a group of program modules that realizes coronary artery analyzing functions. These programs are recorded in the storage, loaded into the memory when booted up, and executed by the processor. Thereby, the diagnosis WS 6 operates as various processing means that include a volume data obtaining means 61, a coronary artery region extracting means 62, a correlation establishing means 63, an index value calculating means 64, an index value integrating means 65, an alert required region detecting means 66, and an output control means 67 illustrated in FIG. 1.

Imaging synchronized with ECG's employing an MSCT apparatus or a DSCT apparatus is performed for examinations of the heart. During imaging synchronized with ECG's, 10 to 20 sets of volume data are obtained within a single cardiac cycle, and output as files.

Hereinafter, imaging synchronized with ECG's will be described with reference to FIG. 2. The upper portion of FIG. 2 represents the waveform of an ECG. In the ECG, the period between a first R wave and a next R wave corresponds to a single cardiac cycle. Positions along the horizontal axis (temporal axis) of the ECG are phases, which are represented as percentages by dividing the single cardiac cycle into 100. For example, if 10 sets of volume data are obtained during the single cardiac cycle at equal intervals, the phases represented by each set of volume data are: R-R0%, R-R10%, R-R20%, R-R30%, . . . R-R90%. Note that although there are differences in heartbeats among individuals, in many cases, the systolic phase is from R-R0% to about R-R45%, and the diastolic phase is from about R-R45% to R-R100%.

Figure 3B:
FIG. 3B is a diagram that illustrates a heart at a phase R-R10%.
Figure 3C:
FIG. 3C is a diagram that illustrates a heart at a phase R-R20%.
Figure 3D:
FIG. 3D is a diagram that illustrates a heart at a phase R-R30%.
Figure 3E:
FIG. 3E is a diagram that illustrates a heart at a phase R-R40%.
Figure 3F:
FIG. 3F is a diagram that illustrates a heart at a phase R-R50%.
Figure 3G:
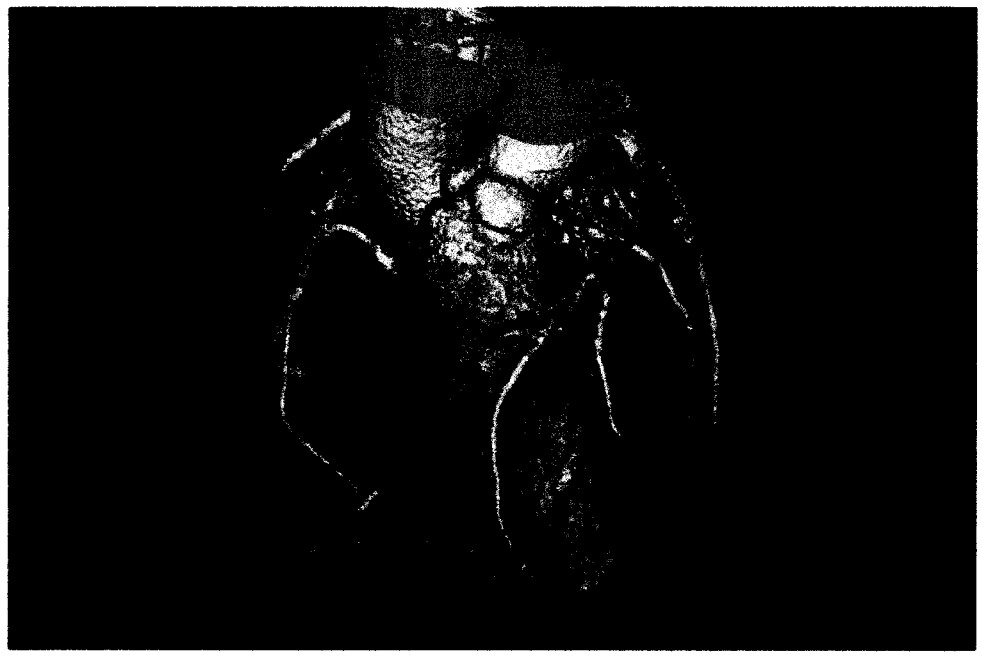
FIG. 3G is a diagram that illustrates a heart at a phase R-R60%.
Figure 3H:
FIG. 3H is a diagram that illustrates a heart at a phase R-R70%.
Figure 3I:
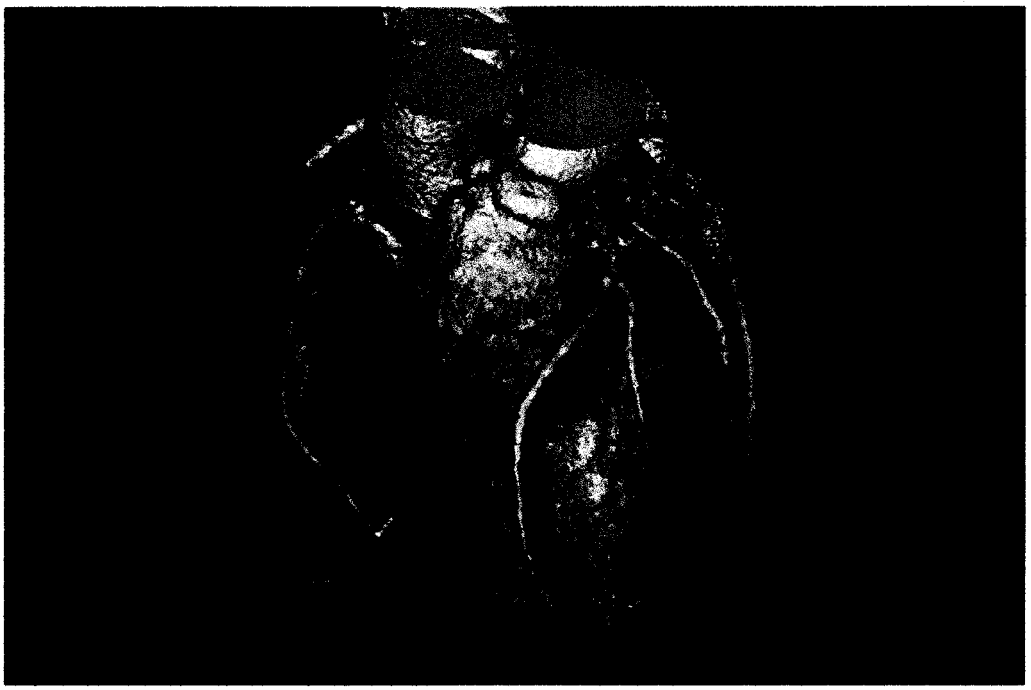
FIG. 3I is a diagram that illustrates a heart at a phase R-R80%.
Figure 3J:
FIG. 3J is a diagram that illustrates a heart at a phase R-R90%.

FIGS. 3A through 3J are diagrams that illustrate examples of sets of volume data obtained by imaging synchronized with an ECG. More specifically, FIGS. 3A through 3J are examples of volume rendered images (hereinafter, referred to as "VR images") which are generated from volume data. FIG. 3A illustrates a heart at R-R0%, FIG. 3B illustrates a heart at R-R10%, FIG. 3C illustrates a heart at R-R20%, FIG. 3D illustrates a heart at R-R30%, FIG. 3E illustrates a heart at R-R40%, FIG. 3F illustrates a heart at R-R50%, FIG. 3G illustrates a heart at R-R60%, FIG. 3H illustrates a heart at R-R70%, FIG. 3I illustrates a heart at R-R80%, and FIG. 3J illustrates a heart at R-R90%. FIGS. 3A through 3J represent a heart as viewed from the front of a human body. The blood vessel along the wall of the heart toward the left in the drawings is the right coronary artery, and the blood vessel along the wall of the heart toward the right in the drawings is the left coronary artery.

As is clear from the examples of FIGS. 3A through 3J, the ease with which coronary artery regions can be discriminated within VR images differ among the phases. In addition, the ease with which coronary artery regions can be discriminated differ within a single VR image, according to the positions and the thicknesses of the coronary artery. For example, the tips of the coronary arteries are cut off and difficult to discriminate in FIG. 3A (R-R10%) and FIG. 3J (R-R90%), but can be clearly discriminated in FIG. 3G (R-R30%). In addition, the root portion of the right coronary artery is clear in FIG. 3D (R-R30%). However, the boundary between the coronary artery region and the cardiac muscle region is unclear in FIG. 3F, and difficult to discriminate. For these reasons, it is difficult to select a single phase which is optimal to discriminate regions in.

Even assuming that a single optimal phase for discriminating regions is selected from among the examples of FIGS. 3A through 3J, sets of volume data of that phase will not always be optimal for discriminating regions in. This is because there are differences in the shapes of hearts and the movement of the cardiac muscles among individuals, as described previously. Although FIGS. 3A through 3J are merely examples, it is often the case that sets of volume data obtained by imaging synchronized with ECG's have similar problems.

Hereinafter, the processes which are performed by each of the means that constitute the diagnosis WS 6 will be described. If the function for assisting diagnosis of coronary arteries is selected in an initial screen, and the ID number of a patient or an examination number is input, the volume data obtaining means 61 transmits the input data to the data server 4, to request search and transfer files which are stored in the high capacity storage 5. The files for which transfer is requested may be files that represent specific phases. The range of phases to be requested may be defined in setting data in advance, or may be specified by a user by providing a predetermined user interface.

The data server 4 searches the files within the high capacity storage 5 and transfers the requested group of files to the volume data obtaining means 61 in response to the aforementioned request. If specific phases are not specified in the request, the data server 4 transfers all files which are obtained during a single cardiac cycle. On the other hand, if specific phases are specified, the data server 4 transfers only files that represent the specified phases. The volume data obtaining means 61 stores the volume data included in the files transferred from the data server 4 into the memory.

The coronary artery region extracting means 62 extracts coronary artery regions, that is, the walls and the intravascular regions of the coronary arteries, from each of the sets of volume data stored in the memory by the above process. In addition, the paths of the coronary arteries are specified during the process for extracting the coronary artery regions. These processes may be performed with respect to all of the supplied volume data. Alternatively, these processes may be performed only with respect to sets of volume data that represent specific phases. The targets of these processes (the range of phases to be processed) may be defined in advance in setting data, or may be specified by a user by providing a predetermined user interface.

In cases that processing efficiency is prioritized, it is preferable for the number of sets of data to be processed to be reduced, by the processing targets being narrowed by the volume data obtaining means 61 or by coronary artery region extracting means 62 as described above. The number of sets of data may be reduced by thinning 20 sets of data are obtained at phase intervals of 5% by selecting 10 sets of volume data at phase intervals of 10%, for example. Alternatively, sets of volume data which are effective for analysis, such as those obtained during a telesystolic phase and a mid-diastolic phase may be selected, while sets of volume data that represent other phases are excluded.

Hereinafter, the process for extracting the coronary artery regions will be described further. Various methods for extracting coronary artery regions from volume data have been proposed. An example of such a method is that disclosed in A. Szymczak et al., "Coronary Vessel Trees from 3D Imagery: A Topological Approach", Medical Image Analysis, Vol. 10, Issue 4, pp. 548-559, 2006. Any known method can be applied to extract the coronary artery regions. However, the present embodiment employs the method proposed by the present applicant in Japanese Patent Application Nos. 2009-048679 and 2009-069895. The outline of the process described in these documents will be described hereinbelow.

Figure 4:
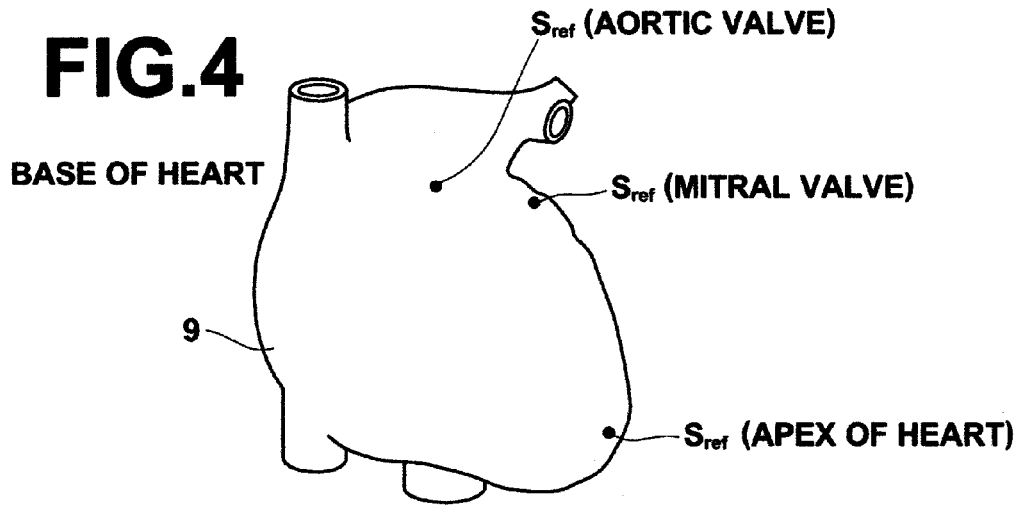
FIG. 4 is a diagram that illustrates an example of a cardiac region extracted by a coronary artery region extracting means.

The coronary artery region extracting means 62 extracts a region corresponding to the heart (hereinafter, referred to as a "cardiac region") from volume data based on a predetermined algorithm. FIG. 4 is a diagram that illustrates an example of a cardiac region 9 extracted by the coronary artery region extracting means 62. Positions Sref of points that characterize the shape of the heart, such as the position of the aortic valve, the position of the mitral valve, and the position of the apex of the heart, are also specified during the process for extracting the cardiac region 9. The coordinates of the specified positions are stored in the memory, and utilized to define a reference coordinate system in processes to be described later.

Figure 5:
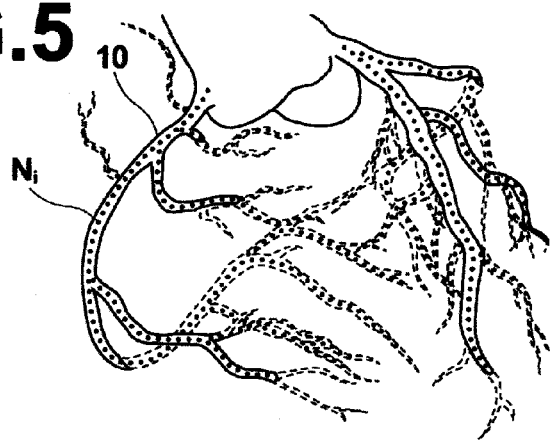
FIG. 5 is a diagram that illustrates examples of candidate points detected by the coronary artery region extracting means.

Next, a rectangular parallelepiped region that includes the cardiac region 9 is set as a search range, linear structures are searched for within the search range based on a predetermined algorithm. Further, points which are estimated to be points along the cores of coronary arteries are detected, based on the linear structures detected by the search. In the following description, the points which are estimated to be points along the cores of coronary arteries will be referred to as candidate points or nodes. FIG. 5 illustrates an example of a linear structure 10 and detected candidate points Ni.

The search for the linear structures is performed by calculating eigenvalues of a 3×3 Hessian matrix for each local region within the search range. In regions that include linear structures, one of the three eigenvalues of the Hessian matrix becomes a value close to zero, while the other two values will be relatively greater values. In addition, the eigenvector that corresponds to the eigenvalue close to zero indicates the direction of the main axis of the linear structures. The coronary artery region extracting means 62 utilizes this relationship to judge likelihoods of being linear structures based on the eigenvalues of a Hessian matrix for each local region. In local regions in which linear structures are discriminated, the center points thereof are detected as candidate points.

Note that it is preferable for the resolution of the data within the search range to be converted to generate a plurality of sets of data having different resolutions (a Gaussian pyramid), and to repeatedly perform searches (scans) at different resolutions. In the search method described above, it is not possible to discriminate linear structures in cases that the diameters (widths) of local regions are smaller than the diameters of blood vessels. However, it will become possible to discriminate linear structures of various sizes by performing searches in different resolutions. Thereby, candidate points can be thoroughly detected for thick blood vessels at the root portions and thin blood vessels at the tips.

Figure 6:
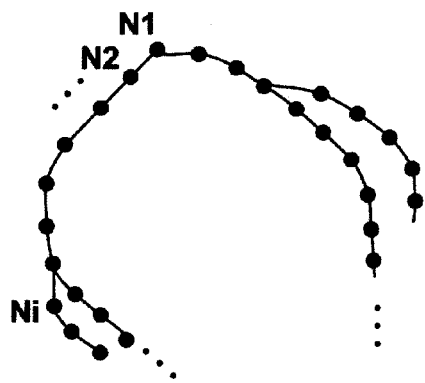
FIG. 6 is a diagram that illustrates an example of a tree structure constructed by linking extracted candidate points.

Next, the candidate points which are detected by the search are linked based on a predetermined algorithm. Thereby, tree structures constituted by the candidate points and blood vessel branches (edges) that connect the candidate points are constructed, as illustrated in FIG. 6. The coordinate data of the detected plurality of candidate points and vector data that represent the directions of the blood vessel branches are stored in the memory, along with identifiers for the candidate points and the blood vessel branches.

Next, the shapes of the coronary arteries are discriminated in detail based on the values of the surrounding voxels (CT values) for each detected candidate point. More specifically, the outlines (the outer walls of the blood vessels) of the coronary arteries are discriminated within cross sections perpendicular to the pathways of the coronary arteries. The discrimination of shapes is performed employing a known segmentation method, such as the Graph Cuts method.

Figure 7:
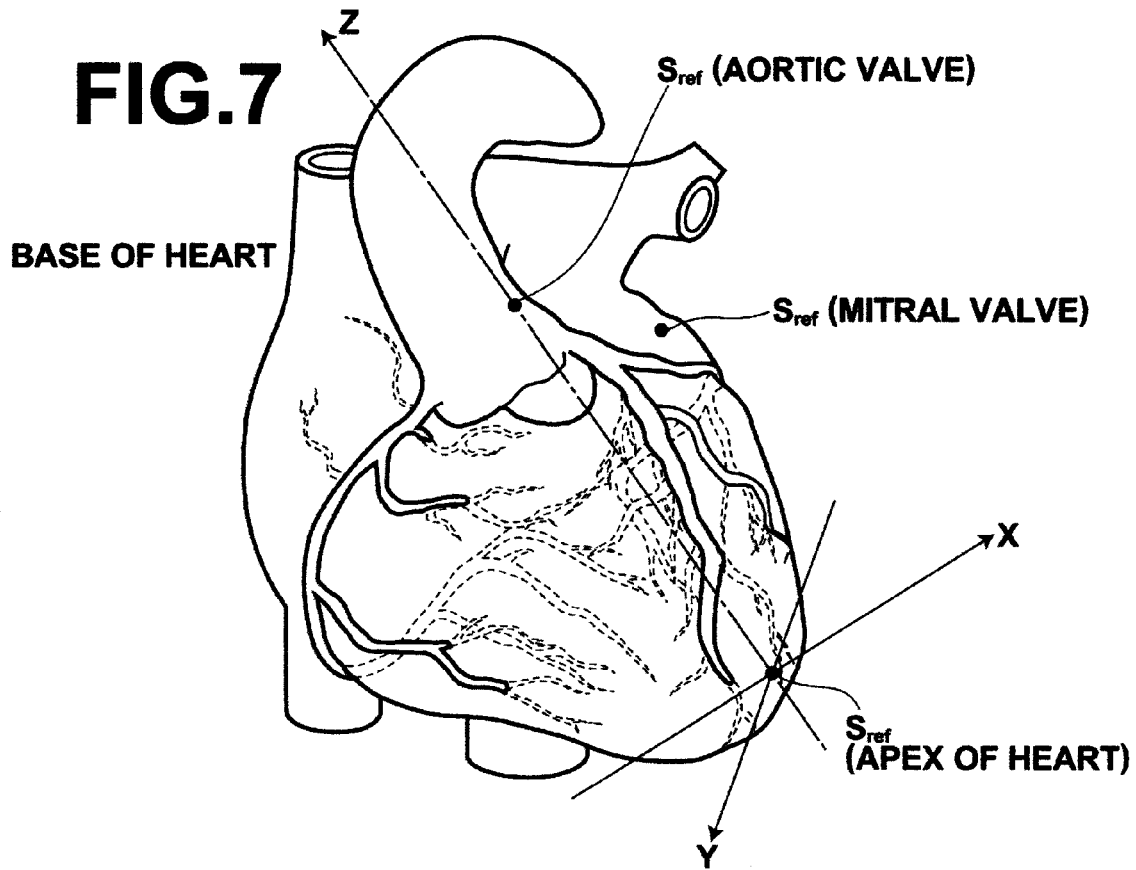
FIG. 7 is a diagram that illustrates an example of a reference coordinate system.

Finally, the coronary artery region extracting means 62 defines a reference coordinate system, in which the positions Sref of the aortic valve, the mitral valve, and the apex of the heart which were stored in the process for discriminating the cardiac region 9 are designated as reference positions. For example, the apex of the heart is set as the origin of the reference coordinate system, the direction from the apex of the heart toward the aortic valve is designated as a Z axis, and the X and Y axes are defined based on the relationship with the mitral valve, as illustrated in FIG. 7. In addition, the scale of the coordinate system is normalized by defining the distance from the apex of the heart to the aortic valve as 1. Then, the coordinate values which were recorded in the memory by the aforementioned processes are converted to coordinate values within the reference coordinate system. That is, data that represent the positions of the candidate points and the branches, the outlines of the coronary arteries, and the like are normalized. The normalized data are correlated with data prior to normalization, and stored in the memory. The normalized data regarding the candidate points and the outlines will be referred to as coronary artery region data in the following description.

Next, the processes which are performed by the correlation establishing means 63 will be described. As described above, the processes which are performed by the coronary artery region extracting means 63 are performed with respect to a plurality of sets of volume data which are obtained during different phases. Accordingly, a plurality of sets of coronary artery region data are obtained for coronary arteries for a single heart.

Figure 8:
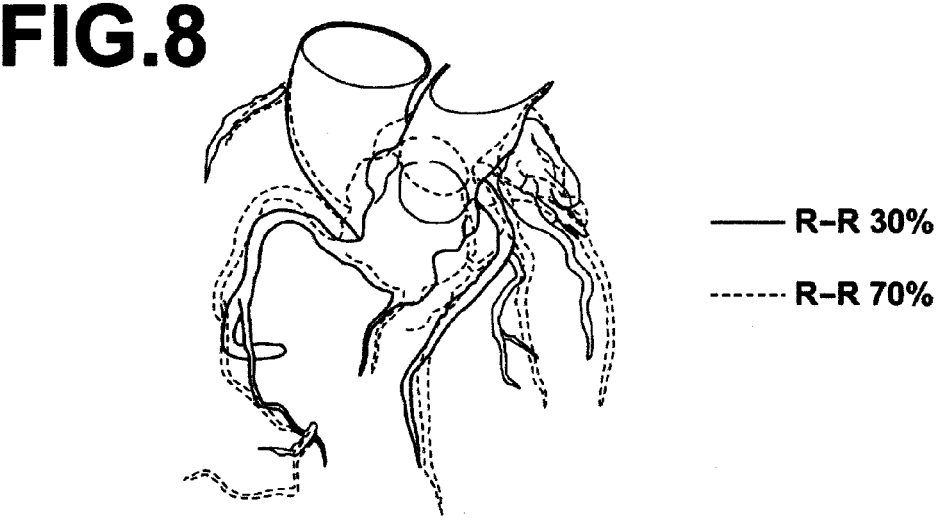
FIG. 8 is a diagram for explaining the differences in the paths of coronary arteries during different phases.

The positions and shapes of the coronary arteries change accompanying the beating of the heart. Therefore, the candidate points which are detected within sets of volume data that represent different phases will not always have the same positional coordinates, even if they are positioned at the same anatomical points. For example, FIG. 8 is a diagram in which the main portions of the coronary artery regions in FIG. 3D (R-R30%) and FIG. 3H (R-R70%) are overlapped on each other. As illustrated in FIG. 8, the paths of the coronary arteries differ during the systolic phase and the diastolic phase.

Figure 9:
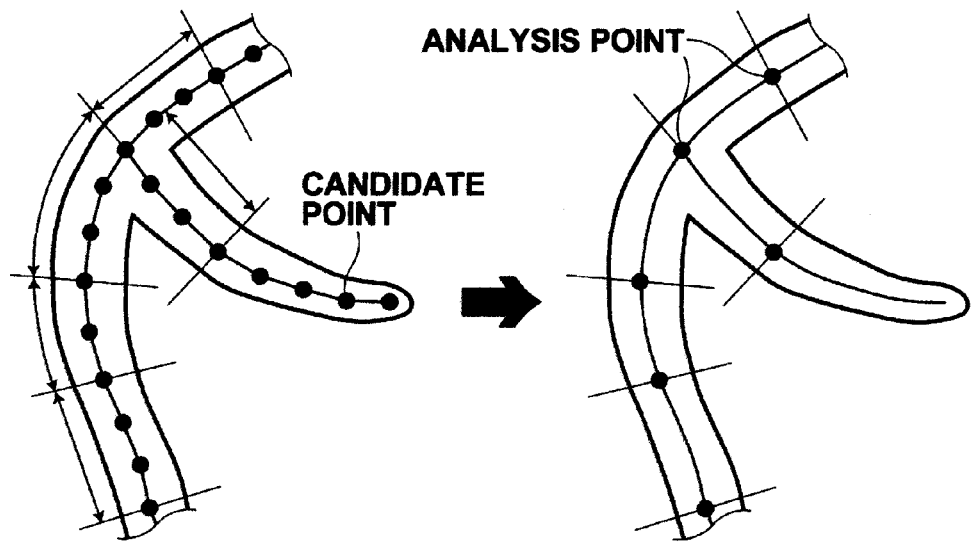
FIG. 9 is a diagram that illustrates examples of set analysis points.

The correlation establishing means 63 establishes correlations among the plurality of sets of coronary artery region data obtained with respect to the coronary arteries of a single heart. More specifically, correlations are established among candidate points which have different positional coordinates within the reference coordinate system but are positioned at the same anatomical points. Correlations may be established among all of the candidate points that constitute the tree structures. However, in the present embodiment, a portion of the candidate points are set as analysis points as illustrated in FIG. 9, and correlations are established only among the set analysis points. The analysis points are set by the following process.

The correlation establishing means 63 divides the tree structures which are specified by the candidate points and the branches into segments. In the present embodiment, candidate points which are linked to three or more branches, that is, candidate points which are positioned at branching points, are set as the boundaries of the segments. Further, candidate points and branches that extend beyond the branching points are divided into segments having a predetermined number of candidate points or segments having a predetermined length. Then, the candidate points which are positioned at the boundaries of each segment are selected as the analysis points. The analysis points are set by the correlation establishing means 63 storing data necessary to specify the analysis points (the positional coordinates or identifiers of the candidate points).

Figure 10:
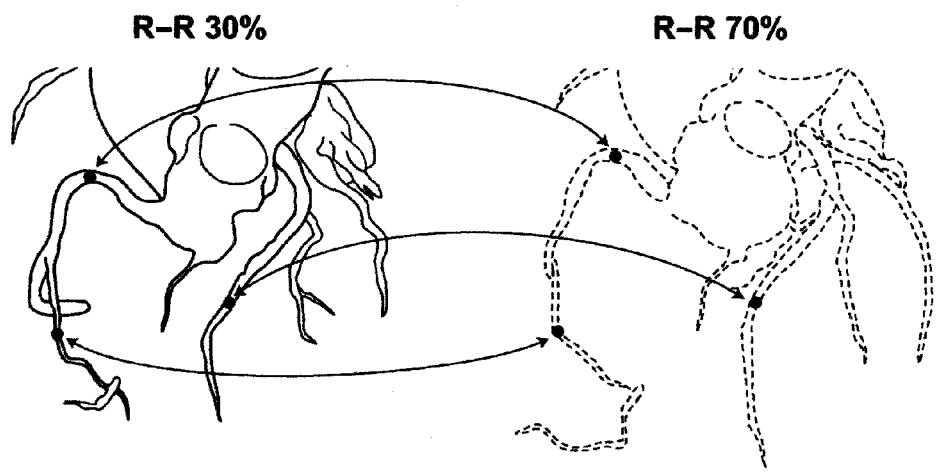
FIG. 10 is a diagram for explaining a process performed by a correlation establishing means.

After the analysis points are set, the correlation establishing means 63 establishes correlations among analysis points which are estimated to be at the same anatomical points by a graph matching technique. In the present embodiment, the correlation establishing means 63 calculates degrees of similarity among analysis points which are set along the paths of coronary arteries based on a predetermined evaluating function, and establishes correlations among analysis points having the highest degrees of similarity. The evaluating function is defined, taking the positional coordinates within the reference coordinate system, the numbers and coordinate values of the candidate points which are linked to the analysis points, the diameters of the blood vessels in the periphery of the analysis points, etc., into consideration. At this time, it is preferable for the number and the types of elements to be considered to be set while considering a balance between the accuracy of evaluations and processing time. According to this technique, analysis points which are positioned at the same anatomical points can be correlated with each other even if the shapes and the positions of coronary arteries differ during the systolic phase and the diastolic phase, as illustrated in FIG. 10.

Note that various methods have been proposed with respect to establishing correlations among anatomical structures by a graph matching method, as exemplified in U.S. Pat. No. 7,646,903. Other known techniques may be employed to establish correlations among the analysis points.

Figure 11A:
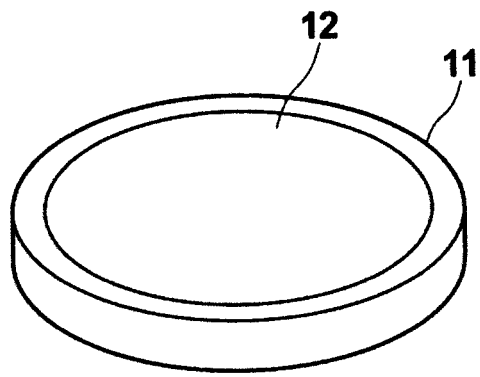
FIG. 11A is a diagram that illustrates a cross section of a coronary artery region without plaque.
Figure 11B:
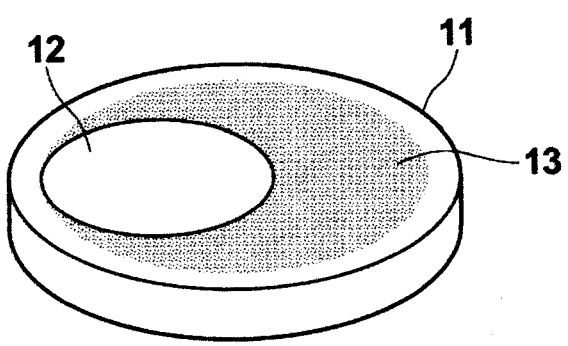
FIG. 11B is a diagram that illustrates a cross section of a coronary artery region with plaque.

Next, the processes which are performed by the index value calculating means 64 will be described. The index value calculating means 64 calculates an index value that indicates the character of plaque at each analysis point within each of the plurality of coronary artery regions extracted by the coronary artery region extracting means 62. FIG. 11A and FIG. 11B are diagrams that illustrate cross sections of coronary arteries at analysis points, wherein FIG. 11A illustrates a normal coronary artery, and FIG. 11B illustrates a coronary artery having plaque deposits on the inner walls thereof.

First, the index value calculating means 61 discriminates an intravascular region 12 and a plaque region 13 within a coronary artery region 11. Generally, the CT values of soft plaque are lower than the CT values of a normal intravascular region, and the CT values of hard plaque are higher than the CT values of a normal intravascular region. In MRI's as well, it is known that signal values for plaque are outside the range of signal values for normal intravascular regions. Therefore, the index value calculating means 64 utilizes this relationship among signal values to distinguish plaque regions and intravascular regions. More specifically, the value of each voxel that constitutes cross sections is compared against predetermined threshold values, to judge whether the voxels represent plaque or intravascular regions. A region constituted by voxels which have been judged to represent plaque is designated as the plaque region 13, and a region constituted by voxels which have been judged to represent an intravascular region is designated as the intravascular region 12. Note that plaque is also classified into soft plaque and hard plaque.

Figure 12:
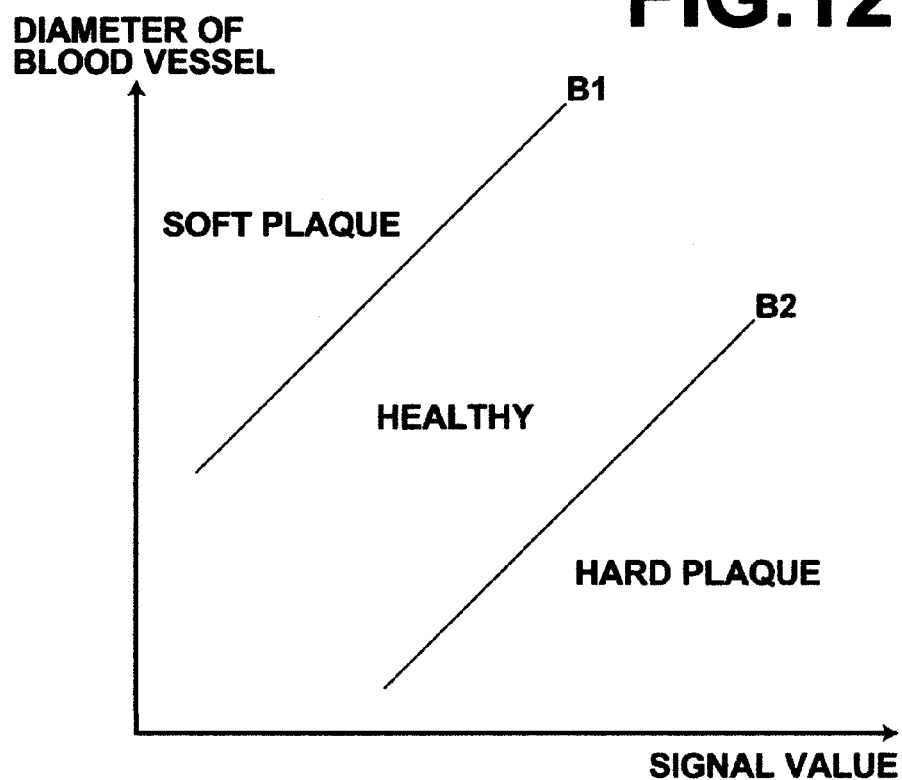
FIG. 12 is a diagram for explaining a method by which regions are judged.

Here, the range of possible signal values that represent intravascular regions depends on the thickness of blood vessels and imaging conditions, and therefore is not constant. For this reason, it is preferable for the threshold values which are employed to distinguish plaque regions and intravascular regions to be values that change according to the thicknesses of blood vessels. In the present embodiment, as illustrated in FIG. 12, the threshold values are set as two borderlines B1 and B2 that divide the plane of a coordinate having signal values as the horizontal axis and the diameters of blood vessels (average diameters or average radii measured in a plurality of directions) as the horizontal axis into three sections. These borderlines are set by performing learning in advance, using sample data that represent normal blood vessels and blood vessels with plaque deposits having different thicknesses. The set borderlines are stored in the memory, and referred to by the index value calculating means 64.

The index value calculating means 64 judges whether voxels represent soft plaque, hard plaque, or an intravascular region, based on which sides of the borderlines B1 and B2 coordinate points (signal values of the voxels and the diameter of blood vessels) on the coordinate plane of FIG. 12 are positioned. The thicknesses of blood vessels are in a correlative relationship not only with the diameters of blood vessels, but also with the areas thereof. Therefore, the vertical axis of the coordinate plane for setting the borderlines may alternatively be the areas of blood vessels.

Next, the index value calculating means 64 calculates two index values that indicate the character of plaque. A first index value I1 is the percentage of the coronary artery region that plaque occupies, that is, the stenosis rate. The first index value I1 is calculated by Formula (1) below. In Formula (1), Aplaque is the area of the plaque region 13, and Aall is the area of the coronary artery region 11. Alternatively, Aall may be a combined area of the plaque region 13 and the intravascular region 12. Note that the area of each of the regions can be derived based on the number of voxels that constitute the region.

$$I1 = Aplaque/Aall \cdot 100 \quad (1)$$

A second index value I2 is a value that represents the likelihood that plaque is unstable. Among plaque which adheres to the walls of blood vessels, soft plaque is more unstable compared to hard plaque. Therefore, it is said that the risk of thrombosis occurring due to plaque breakdown is more likely to occur with soft plaque compared to hard plaque. The index value I2 becomes high in cases that the signal values of plaque regions are low (soft plaque) and becomes low in cases that the signal values of plaque regions are high (hard plaque). For example, a value of 1 is output as the index value I2 if the average signal value of a plaque region is positioned toward the left of the borderline B1; a value of 0.5 is output as the index value I2 if the average signal value of a plaque region is positioned toward the right of the borderline B2; and a value of 0 is output if no plaque regions are present.

In addition, the index value calculating means 64 may output a value obtained by multiplying the index value I1 by the index value I2 as a third index value I3. Note that the index values which are calculated by the index value calculating means 64 are not limited to the examples described above. Other examples of index values include index values that indicate judgment results regarding whether plaque is present, index values that indicate characteristics other than instability (for example, hardness), and index values that indicate the components of plaque. In addition, in the example described above, the index values are calculated based on the diameters or the areas of coronary artery regions and the signal values of voxels. However, there are index values that can be calculated based only on the diameters, only on the areas, and only on the signal values. Ratios between the diameters or the areas of coronary artery regions and intravascular regions may be calculated as index values that indicate the degree of stenosis, for example. Alternatively, whether plaque is present may be judged based only on signal values, and the judgment results may be output as index values.

By executing the processes described above for each of the analysis points, index values I1 and I2 are obtained for each of the analysis points for which correlations have been established by the correlation establishing means. For example, in the case that the coronary artery region extracting means 62 executes the coronary artery region extracting process for six phases, 6n values are calculated for each type of index value, as illustrated in Table 1. Although Table 1 illustrates calculation results for index value I1, 6n values are also obtained for index value I2.

TABLE 1

|     | R-R30% | R-R40% | R-R50% | R-R60% | R-R70% | R-R80% |
|-----|--------|--------|--------|--------|--------|--------|
| AP1 | 0      | 0      | 5      | 0      | 0      | 0      |
| AP2 | 0      | 0      | 5      | 0      | 0      | 0      |
| ... | ...    | ...    | ...    | ...    | ...    | ...    |
| APj | 80     | 85     | 80     | 85     | 85     | 80     |
| ... | ...    | ...    | ...    | ...    | ...    | ...    |
| APk | 0      | 0      | 60     | 0      | 0      | 0      |
| ... | ...    | ...    | ...    | ...    | ...    | ...    |
| APn | 0      | 5      | 0      | 5      | 5      | 0      |

Note that in Table 1 and the following description, the plurality of analysis points which are set along the paths of coronary arteries in phases R-Rx % ($0 \leq x < 100$, x represents a phase) and correlated with each other are expressed as apxi ($0 < i \leq n$, i represents an identifier of each analysis point, and n represents the number of analysis points). In addition, points which are correlated and recognized as being points at the same anatomical position are expressed as APi. The point APi represents a single anatomical point, but is a group of a plurality of pieces of data, and APi={ap00i, ap10i, . . . , ap80i, ap90i}.

Next, the processes which are performed by the index value integrating means 65 will be described. The index value calculating means 64 performs the index value calculating processes with respect to the analysis points apxi, which are set within each of the coronary artery regions. For this reason, the index value calculating means 64 calculates a plurality of index values for points (cross sections) which are positioned at the same anatomical points. The index value integrating means 65 derives a single integrated evaluation value for each analysis point APi, by integrating the plurality of index values which are output by the index value calculating means 64.

In the present embodiment, the index value integrating means 65 calculates weighted averages of the plurality of index values I1 and I2 by obtaining weighted averages of the index values which have been calculated for each phase, and outputs the weighted averages as evaluation values. Here, evaluation values which are derived from the index values I1 will be expressed as V1, and evaluation values which are derived from the index values I2 will be expressed as V2. Evaluation values V1APi for the points APi can be calculated by Formula (2) below.

$$V1_{APi} = \sum_{x} \alpha_x \times I1_{xi} \quad (2)$$

wherein $\alpha_x$ is a weighting coefficient set for a phase R-Rx %, and $I1_{xi}$ ($0 < i \leq n$) is each of the index values I1 calculated for analysis points apxi along the path of the coronary arteries in the phase R-Rx %.

Values of the weighting coefficients $\alpha_x$ for all possible phases are registered in the memory in advance. In the present embodiment, combinations of a plurality of weighting coefficients are registered, and the weighting coefficients can be switched by a user performing a selecting operation. Table 2 illustrates an example of settings of weighting coefficients $\alpha_x$. Note that the numerical values shown in Table 2 are merely examples.

TABLE 2

|  | R-R0% | R-R10% | R-R20% | R-R30% | R-R40% | R-R50% | R-R60% | R-R70% | R-R80% | R-R90% |
|---|---|---|---|---|---|---|---|---|---|---|
| S1 | 0 | 0 | 0 | 0.05 | 0.4 | 0.05 | 0.05 | 0.4 | 0.05 | 0 |
| S2A | 0 | 0 | 0 | 0 | 0 | 0 | 0.3 | 0.4 | 0.3 | 0 |
| S2B | 0 | 0 | 0 | 0.3 | 0.4 | 0.3 | 0 | 0 | 0 | 0 |

In Table 2, setting example S1 sets the weighting of phases other than the telesystolic phase and the middiastolic phase to 0, and places high weighting coefficients with respect to phases R-R40% and R-R70%. The index values calculated for phases in which the influence of motion artifacts, etc. are less likely to occur are heavily weighted, while the index values calculated for the other phases are lightly weighted. Thereby, the reliability of the calculated evaluation values can be improved.

In addition, in Table 2, setting example S2A enables obtainment of evaluation values only from index values calculated for the telesystolic phase (R-R70% and the vicinity thereof), while setting example S2B enables obtainment of evaluation values only from index values calculated for the middiastolic phase (R-R40% and the vicinity thereof). Using these examples, the index values which are calculated for analysis points set within the left coronary artery region may be multiplied by the weighting coefficients of setting example S2A, and the index values which are calculated for analysis points set within the right coronary artery region may be multiplied by the weighting coefficients of setting example S2B. Thereby, the reliability of the calculated evaluation values can be further improved.

The alert required region detecting means 66 detects regions at which alerts are required, based on the evaluation values V1APi and V2APi calculated by the index value integrating means 65. In the present embodiment, if at least one of the evaluation values V1APi and V2APi calculated for an analysis point APi is greater than threshold values stored in a memory, the analysis point APi is detected as an alert required region. That is, regions at which the stenosis rate is high are judged as alert required regions even if plaque is stable, and regions at which the instability of plaque is high are judged as alert required regions even if the stenosis rate is low. It goes without saying that regions having both high stenosis rates and high instability of plaque are judges as alert required regions. Note that it is preferable for the threshold values to be employed to detect the alert required regions to be determined based on past cases. In addition, the definitions of and the detecting methods for the alert required regions may be appropriately determined according to diagnosis principles, and are not limited to those described above.

Figure 13:
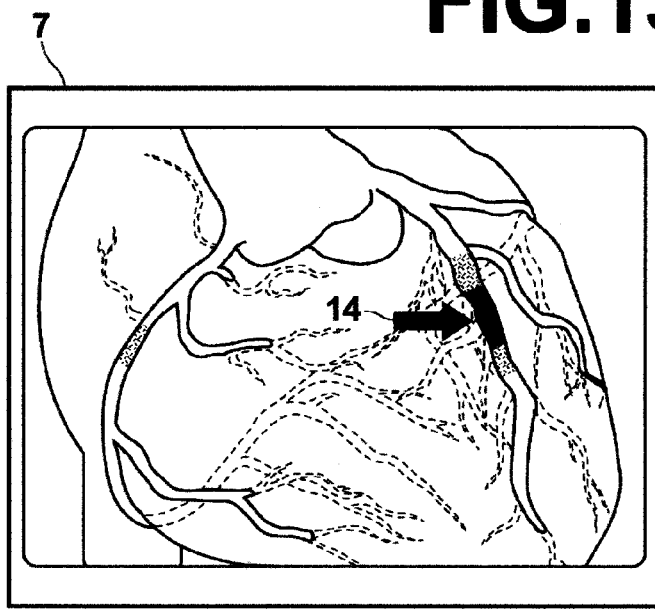
FIG. 13 is a diagram that illustrates an example of a screen output by an output control means.

The output control means 67 outputs the evaluation values of the analysis points and data regarding the alert required regions to the screen of the display 7. FIG. 13 is a diagram that illustrates an example of an output display screen. In the present embodiment, an image of the coronary artery region, which is color coded according to the evaluation values regarding the character of plaque, is generated and displayed on the screen. The image of the coronary artery region to be displayed may be a volume rendered image or a CPR image. Further, a highlighting color such as red is assigned to a region which is judged to be an alert required region, and an arrow 14 that points to the alert required region is also displayed. However, the manner in which the evaluation results and the alert required regions are indicated is not limited to the example illustrated in FIG. 13, and it goes without saying that various modifications are possible.

Note that the output control means 67 may output an image of the display screen, a list of numerical values that indicates the correlations among identifiers of the analysis points and the evaluation values, etc. to a printer or to a recording medium, in addition to outputting the display screen to the display 7.

It is rare for the character of plaque to change suddenly within a single cardiac cycle. Therefore, the index values that represent the character of plaque should fundamentally be approximately equal, as in point APj of Table 1. However, there are cases in which coronary artery regions cannot be accurately detected from volume data due to poor image quality, and erroneous calculation results are obtained for a portion of the phases, as in point APk of Table 1.

In a conventional method, in the case that the phase R-R50% is selected, the character of plaque cannot be evaluated correctly. In contrast, the present embodiment evaluates the character of plaque based on a plurality of index values which are calculated for a plurality of phases. Therefore, even if a portion of the index values are erroneous, correct evaluation results can be obtained as a whole. In addition, a conventional method requires physicians to select a set of volume data to be utilized for analysis while observing VR images such as those illustrated in FIGS. 3A through 3H. However, it is not necessary to select a single set of data in the method of the present embodiment, and no burden is placed on physicians.

Note that in the embodiment described above, the alert required region detecting means 66 specifies alert required regions in order to lessen the burden placed on physicians during diagnosis. However, the diagnosis WS 6 may simply display the evaluation results regarding the character of plaque, and leave specification of alert required regions to a physician's judgment. That is, an embodiment may be considered in which the diagnosis WS 6 is not equipped with the alert required region detecting means 66.

In addition, the character of plaque is evaluated by calculating the weighted averages of the index values in the embodiment described above. However, embodiments may be considered in which the character of plaque is evaluated by other evaluating methods, such as calculating simple averages and sums of the plurality of index values. The number of sets of volume data which are obtained, the method for selecting sets of volume data prior to extracting the coronary artery regions, the weighting coefficients, etc. may be changed as appropriate according to the specifications of the modality, the examination method, and the symptoms of subjects.

Further, the all of the series of processes from the obtainment of the sets of volume data to output control is performed by the diagnosis WS 6 in the embodiment described above.

Alternatively, the series of processes may be divided among and executed by a plurality of computers.

As described above, the present invention is not limited to the embodiment described above. Various changes and modifications are possible, as long as they do not stray form the spirit and scope of the invention.

What is claimed is:

1. A diagnosis assisting apparatus, comprising:
   one or more processors configured to:
   obtain a plurality of sets of volume data imaged by one or more imaging modalities, each of which represent the state of a beating heart of a single patient in different phases in one cardiac cycle;
   extract a plurality of coronary artery regions from at least two sets of volume data from among the obtained sets of volume data;
   set a plurality of analysis points at the same anatomical positions in each of the extracted coronary artery regions, which have been extracted from the at least two sets of volume data representing the state of the heart of the single patient at different phases, and establish correlations among the plurality of analysis points, which are set at the same anatomical positions among each of the coronary artery regions;
   calculate index values that indicate a character of plaque at each of the plurality of analysis points that have been set within each of the plurality of coronary artery regions;
   evaluate the index values, by integrating the index values, which are calculated at the plurality of analysis points that have been set in each of the coronary artery regions, by performing weighted calculations on the index values; and
   output the evaluated index values correlated with information regarding the anatomical positions.

2. The diagnosis assisting apparatus as defined in claim 1, wherein:
   the one or more processors extract the plurality of coronary artery regions at least with respect to a set of volume data that represents the heart in a telesystolic state, and a set of volume data that represents the heart in a middiastolic state.

3. The diagnosis assisting apparatus as defined in claim 1, wherein:
   the one or more processors calculate weighted averages of the index values calculated for each of the plurality of analysis points by multiplying the index values by weighting coefficients which are set for particular phases, and evaluates the character of plaque based on the values of the weighted averages.

4. The diagnosis assisting apparatus as defined in claim 3, wherein:
   the weighting coefficients that the index values are multiplied by are set higher for analysis points corresponding to positions within a right coronary artery region during the telesystolic phase than for other weighting coefficients set during other phases; and
   the weighting coefficients that the index values are multiplied by are set higher for analysis points corresponding to positions within a left coronary artery region during the middiastolic phase than for other weighting coefficients set during other phases.

5. The diagnosis assisting apparatus as defined in claim 1, wherein:
   the one or more processors calculate the index values based on at least one of the diameter, the area, and the signal values at the plurality of analysis points of at least one of the coronary artery regions and the intravascular regions of coronary arteries.

6. The diagnosis assisting apparatus as defined in claim 1, wherein the one or more processors are further configured to:
   detect alert required regions based on the evaluated index values regarding the character of plaque; and
   cause positions of the detected alert required regions during output of the evaluated index values to be displayed.

7. The diagnosis assisting apparatus as defined in claim 6, wherein:
   the one or more processors detect regions having index values that indicate at least one of a stenosis rate and a plaque condition greater than a predetermined threshold value.

8. The diagnosis assisting apparatus as defined in claim 1, wherein:
   the one or more processors are further configured to cause the evaluated index values to be displayed such that the evaluated index values overlap images that represent the coronary artery region.

* * * * *